(12) United States Patent
Kroll et al.

(10) Patent No.: US 7,413,302 B2
(45) Date of Patent: Aug. 19, 2008

(54) TAN THRU GLASSES

(75) Inventors: Lori Kroll, Crystal Bay, MN (US); Mark Kroll, Crystal Bay, MN (US)

(73) Assignee: Kroll Family Trust, Crystal Bay, MN (US)

( * ) Notice: Subject to any disclaimer, the term of this patent is extended or adjusted under 35 U.S.C. 154(b) by 0 days.

(21) Appl. No.: 11/674,658

(22) Filed: Feb. 13, 2007

(65) Prior Publication Data

US 2007/0126976 A1  Jun. 7, 2007

Related U.S. Application Data

(63) Continuation-in-part of application No. 11/057,949, filed on Feb. 14, 2005, now Pat. No. 7,175,271, which is a continuation of application No. 10/083,844, filed on Feb. 25, 2002, now Pat. No. 6,854,844, which is a continuation of application No. 09/680,484, filed on Oct. 6, 2000, now Pat. No. 6,350,168, which is a continuation of application No. 09/472,495, filed on Dec. 27, 1999, now abandoned, which is a continuation of application No. 08/927,243, filed on Sep. 11, 1997, now Pat. No. 6,007,395.

(51) Int. Cl.
  *G02C 5/14* (2006.01)
(52) U.S. Cl. .......................... 351/111; 351/41; 351/124
(58) Field of Classification Search .............. 351/41, 351/44, 110, 111, 124; 2/15, 426, 431
See application file for complete search history.

(56) References Cited

U.S. PATENT DOCUMENTS

| | | |
|---|---|---|
| 2,418,069 A | 3/1947 | Delano |
| 2,521,205 A | 9/1950 | David |
| 2,653,612 A | 9/1953 | Hoore |
| 3,039,109 A | 6/1962 | Simpson |
| 3,155,982 A | 11/1964 | Baratelli |
| 4,097,947 A | 7/1978 | Kiefer et al. |
| 4,124,904 A | 11/1978 | Matthes |
| 4,154,513 A | 5/1979 | Goulden |
| 4,162,542 A * | 7/1979 | Frank ..................... 2/15 |
| 4,179,547 A | 12/1979 | Allingham et al. |
| 4,200,360 A | 4/1980 | Mutzhas |
| 4,320,744 A | 3/1982 | Fodor et al. |
| 4,498,882 A | 2/1985 | Evert |
| 4,546,493 A | 10/1985 | Bortnick |
| 4,646,366 A | 3/1987 | Nishida et al. |

(Continued)

FOREIGN PATENT DOCUMENTS

DE  4240643  1/1994

(Continued)

*Primary Examiner*—Huy K Mai
(74) *Attorney, Agent, or Firm*—Thomas F. Lebens; Sinsheimer Juhnke Lebens & McIvor, LLP

(57) ABSTRACT

A pair of glasses includes a first lens and a second lens. A frame is adapted to hold and secure the first lens and the second lens. A first bow and a second bow are attached to the frame and are adapted to be secured to ears of a wearer of the glasses. The first bow and the second bow are at least partially translucent to a spectrum of electromagnetic radiation.

32 Claims, 18 Drawing Sheets

U.S. PATENT DOCUMENTS

| | | |
|---|---|---|
| 4,663,785 A | 5/1987 | Comparetto |
| 4,753,239 A | 6/1988 | Vitolo |
| 4,799,908 A | 1/1989 | Lucius et al. |
| 4,834,688 A | 5/1989 | Jones |
| 4,891,855 A | 1/1990 | Cheng-Chung |
| 5,007,109 A | 4/1991 | Wheeler |
| 5,014,366 A | 5/1991 | Discipio, Sr. |
| 5,035,345 A | 7/1991 | Janko et al. |
| 5,066,082 A | 11/1991 | Longstaff |
| 5,184,968 A | 2/1993 | Michalochick et al. |
| 5,311,394 A | 5/1994 | Naab et al. |
| 5,338,239 A | 8/1994 | Cleaveland et al. |
| 5,370,566 A | 12/1994 | Mitchell et al. |
| 5,374,212 A | 12/1994 | Lall |
| 5,382,184 A | 1/1995 | DiForte et al. |
| 5,518,798 A | 5/1996 | Riedel |
| 5,605,482 A | 2/1997 | Choy et al. |
| 5,618,909 A | 4/1997 | Lofquist et al. |
| 5,660,572 A | 8/1997 | Buck et al. |
| 5,662,707 A | 9/1997 | Jinkerson |
| 5,771,493 A | 6/1998 | Proctor |
| 5,911,612 A | 6/1999 | Steger et al. |
| 5,960,476 A | 10/1999 | Danzy |
| 5,964,628 A | 10/1999 | Scanlon et al. |
| 6,007,395 A | 12/1999 | Kroll |
| 6,082,857 A | 7/2000 | Lockhart |
| 6,224,208 B1 | 5/2001 | Pawlowski |
| 6,254,236 B1 | 7/2001 | Fecteau et al. |
| 6,350,168 B1 | 2/2002 | Kroll |
| 6,854,844 B2 * | 2/2005 | Kroll et eal. ............... 351/44 |
| 6,968,574 B2 | 11/2005 | Kroll |
| 7,175,271 B2 * | 2/2007 | Kroll et al. ............... 351/44 |
| 7,270,411 B2 * | 9/2007 | Kroll ............... 351/44 |
| 2005/0190340 A1 | 9/2005 | Waage, II |
| 2005/0206837 A1 | 9/2005 | Toulch |

FOREIGN PATENT DOCUMENTS

| | | |
|---|---|---|
| FR | 2540335 | 8/1984 |

* cited by examiner

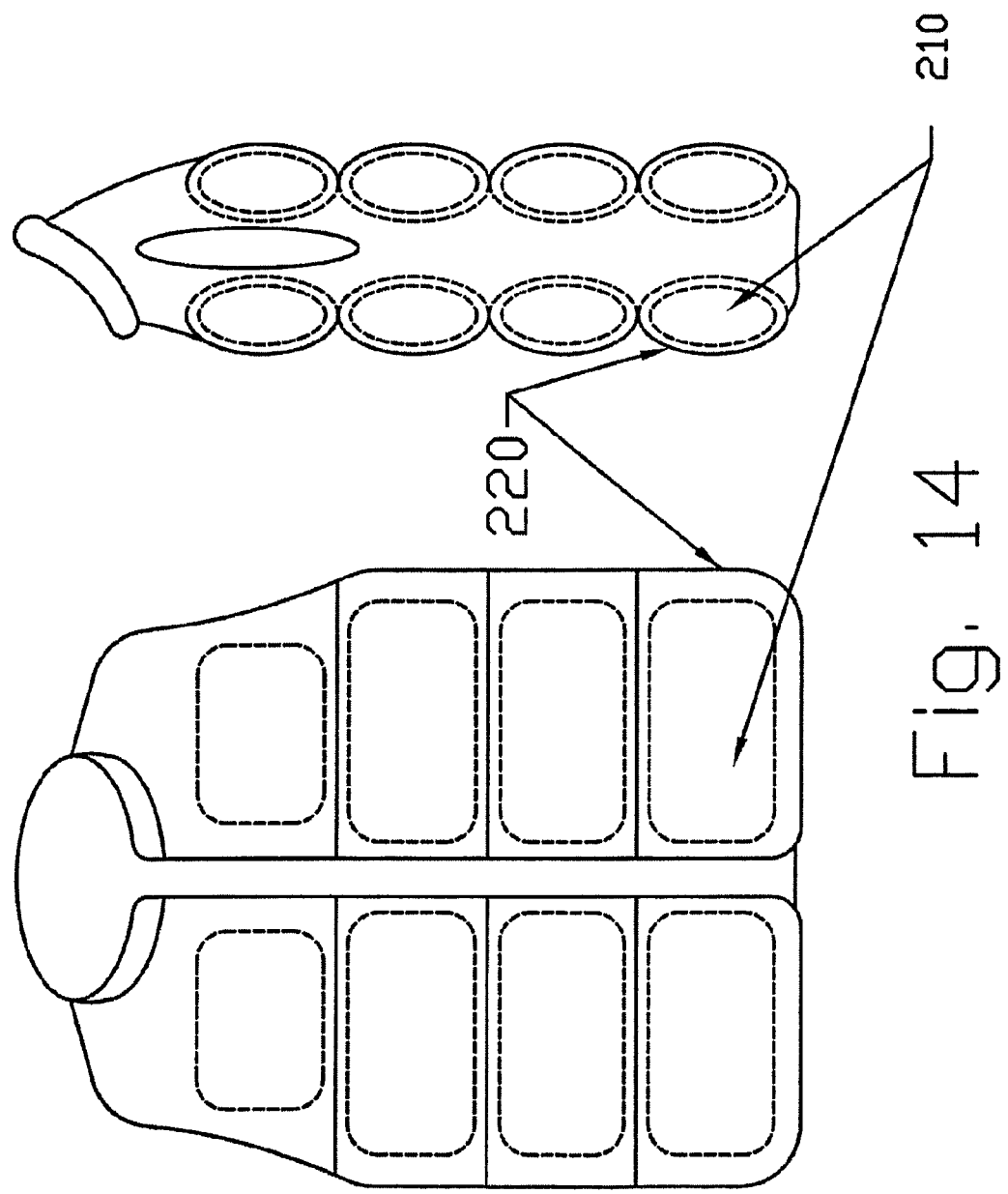

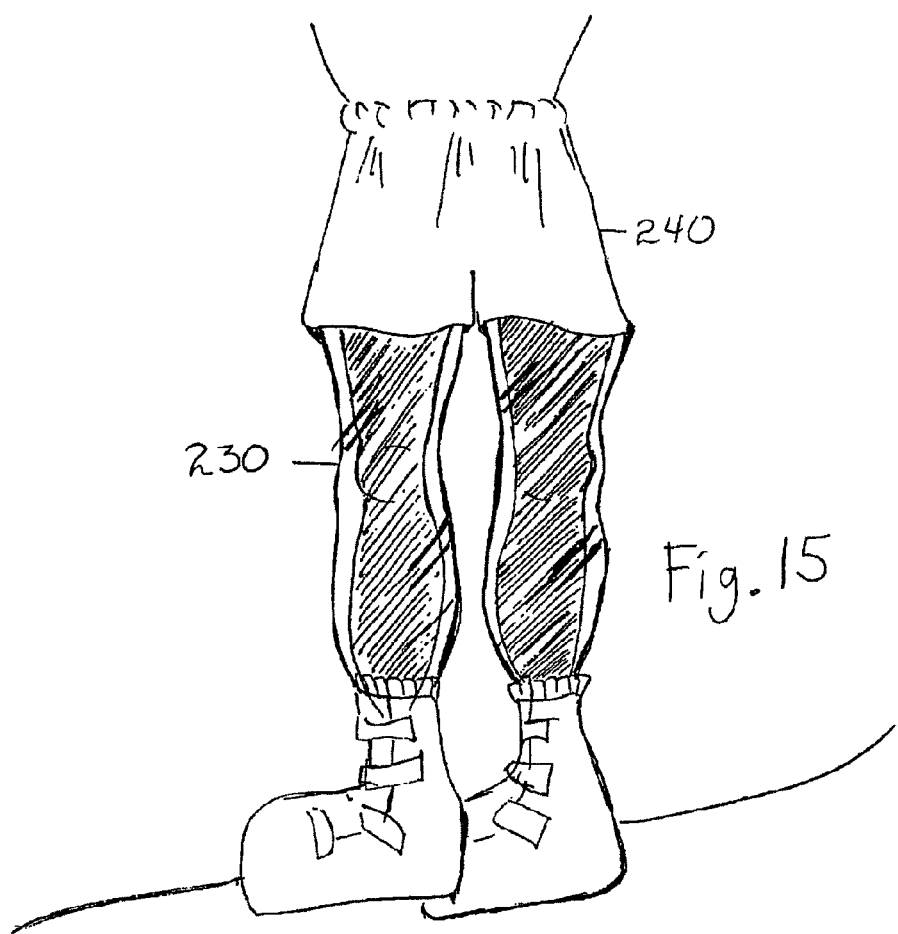

TAN THRU GLASSES

CROSS REFERENCES TO RELATED APPLICATIONS

This application is a continuation-in-part of U.S. application Ser. No. 11/057,949, filed Feb. 14, 2005 and entitled "Tan Thru Glasses," which is a continuation-in-part of U.S. Pat. No. 6,854,844 filed Feb. 25, 2002 and entitled "Tan-Thru Glasses," which is a continuation-in-part of U.S. Pat. No. 6,350,168 filed Oct. 6, 2000 and entitled "Light Selective Sports Garments," which is a continuation-in-part of the application Ser. No. 09/472,495 entitled, "Sun Tanning Life Vest" filed Dec. 27, 1999, now abandoned, which is itself a continuation-in-part of the U.S. Pat. No. 6,007,395 filed Sep. 11, 1997 and entitled "Sun Tanning Life Vest." All of the above patents and applications are hereby incorporated herein by reference in their entirety.

BACKGROUND OF THE INVENTION

People are encouraged to wear life jackets when they are engaged in water sports such a water-skiing, boating, or jet-skiing. However, the same individuals are usually interested in an even suntan. When someone wears a traditional life jacket the area under the life jacket receives no tan and the other areas are very darkly tanned leaving embarrassing lines between the two regions.

Clothing, especially bathing suits, is now available that allows the passage of ultraviolet radiation to facilitate a full body suntan. However, no one has taught a practical life vest that will transmit ultraviolet rays to give an even tan.

There is another issue—aesthetics. An individual may not wish to cover up their body or swimsuit with a light-blocking life vest. Thus, there is a need for a safe and practical life vest that would allow the passage of visible light.

Snow skiers and mountain climbers could also benefit from light selective articles. Garments that would pass heat-carrying ultra-violet radiation but block the loss of the body's infrared radiation would be very useful. Alternatively, garments that would pass visible light would be attractive for the style conscious resort skier that wished to show off their under-jacket garments.

In spite of the numerous possible uses for light selective sport garments there have been none taught beyond the famous light transmitting swimsuit invention of Reidel (U.S. Pat. No. 5,518,798). Reidel's fabric is actually not light transparent but based on the clever trick of a very loose fabric (hexagonal weave) so that only ⅓ of the skin is covered. Camouflage patterns on the suit then provide privacy by preventing the discernment of small physical features. Bortnick (U.S. Pat. No. 4,546,493) taught another swimsuit approach with a conventional rectangular weave but with coated fibers.

Other mentions of light passage in garments have been directed essentially to novelties. Danzy (U.S. Pat. No. 5,960,476) teaches a transparent patch in part of a garment to better display tattoos. Jones (U.S. Pat. No. 4,834,688) teaches a transparent pouch sewn onto a T-shirt to hold, for example, a liquid appearing like beer. Wheeler (U.S. Pat. No. 5,007,109) teaches what are essentially sunglasses attached to a cap.

SUMMARY OF THE INVENTION

The basic object of this invention is the use of light selective materials and fabrics to increase the utility of a garment or sports article. The invention is the novel idea that light selective materials and fabrics can radically improve the usefulness, pleasure, and appeal obtained from sportswear and other garments.

To illustrate the broad applications of this concept the following Table I may be useful by depicting a few examples:

TABLE I

Sample Uses of the Invention

| Light wavelengths | Infrared | Visible | UV-A | UV-B | Gas Filler |
|---|---|---|---|---|---|
| Tan-Thru ™ life vest | optional | Block | Pass | Block | Yes |
| Fast-Tan ™ life vest | Optional | Block | Pass | Pass | Yes |
| See-Thru ™ life vest | Optional | Pass | Block | Block | Yes |
| See & Tan-Thru ™ life vest | Optional | Pass | Pass | Block | Yes |
| Greenhouse Ski Vest | Block | Block | Pass | optional | optional |
| Show-Me ™ Ski Vest | Block | Pass | optional | optional | No |
| Air-Bag ™ ski pants | Optional | Pass | optional | optional | No |

For a Tan-Thru life vest one would prefer to transmit UV-A for the skin tanning properties but to limit the UV-B. The visible light is blocked for reasons of modesty and consumer choice. For the infrared radiation, we have two choices which can actually correspond to two different products. For colder and cloudy weather we would want to hold the infrared radiation within the body so we would block it to keep the wearer as warm as possible. This also reduces cancer risk as infrared can be carcinogenic. For sunny but chilly weather, when there is more infrared from the sun, we may wish to transmit this infrared heat to warm the user short-term. All of the life vests are either permanently or temporarily filled with a gas (including air or a foam material) to provide flotation.

For the Fast-Tan™ life vest, the UV-B would also be passed as the UV-B is a strong promoter of melanization.

For the See-Thru™ life vest, the visible light is passed but both of the UV wavelengths are blocked. The infrared treatment is optional as discussed above. For the See & Tan-Thru™ life vest both visible and UV-A light are transmitted but the UV-B is blocked.

The Greenhouse™ snow-ski vest (alternatively a coat with full length sleeves) would transmit UV-A as it provides high energy heating at high altitudes. The warm body then attempts to retransmit infrared (being of lower temperature than the sun and hence giving off lower frequency photons) which is blocked. Visible light is blocked to allow for the more modest consumer. The UV-B passage is optional. Blocking this reduces ultraviolet damage to light sensitive clothing beneath the vest. Gas filling is optional as it presents more insulation but also more bulk. Note that a single layer of UV-A passing material, that blocks IR, can warm the user without any gas filling being required.

The Show-Me™ ski vest or jacket passes visible light to allow the wearer to reveal clothing or physique beneath. The infrared is blocked to retain heat. The UV-A passage is optional depending on the amount of warming desired. No gas filler is indicated for this device.

The Air-Bag™ snow ski pants are gas filled. They offer light weight warmth and cushioning for falls. They protect the hips from falls as air is a very good shock absorber. They would pass visible light to prevent apparent bulk. Other light wavelength passage choices are optional.

It should be clear from the above samples that this invention presents a major new avenue in sport garments. The chart gives seven samples. However, if one were to amplify on this by considering more possible choices, the number of possibilities are impressive. For example, with the five choices of light wavelength transmission and gas filling there are 32=2*2*2*2*2 combinations. There are many choices for the garment or sport article to apply this invention to. Just counting the following: life vest, snow ski vest, snow ski jacket, snow ski pants, hat, gloves, umbrella, and tent gives 10 choices. Multiplying the 10 choices by the 32 combinations gives us 320 illustrations of this invention. The reader will appreciate that it is not necessary to list every one of these applications.

Beyond that flexibility, there are choices and materials that would divide the various light frequencies into different bands. For example, one might pass the lower frequency part of UV-B (310-320 nm wavelength) while blocking the more dangerous UV-B which has the 290-310 nm wavelengths. This would allow stimulation of tanning without the higher cancer risk of the full UV-B band.

A significant feature of this invention is sunglasses and vision-improving eyeglasses which prevent or reduce the unsightly untanned lines across the temple of the head.

BRIEF DESCRIPTION OF THE DRAWINGS

FIG. 14 shows the use of gas pockets distinct from the outside fabric.

FIG. 15 shows the "Air-Bag" inflated pants embodiment.

DETAILED DESCRIPTION OF THE PREFERRED EMBODIMENTS

Figure 1:
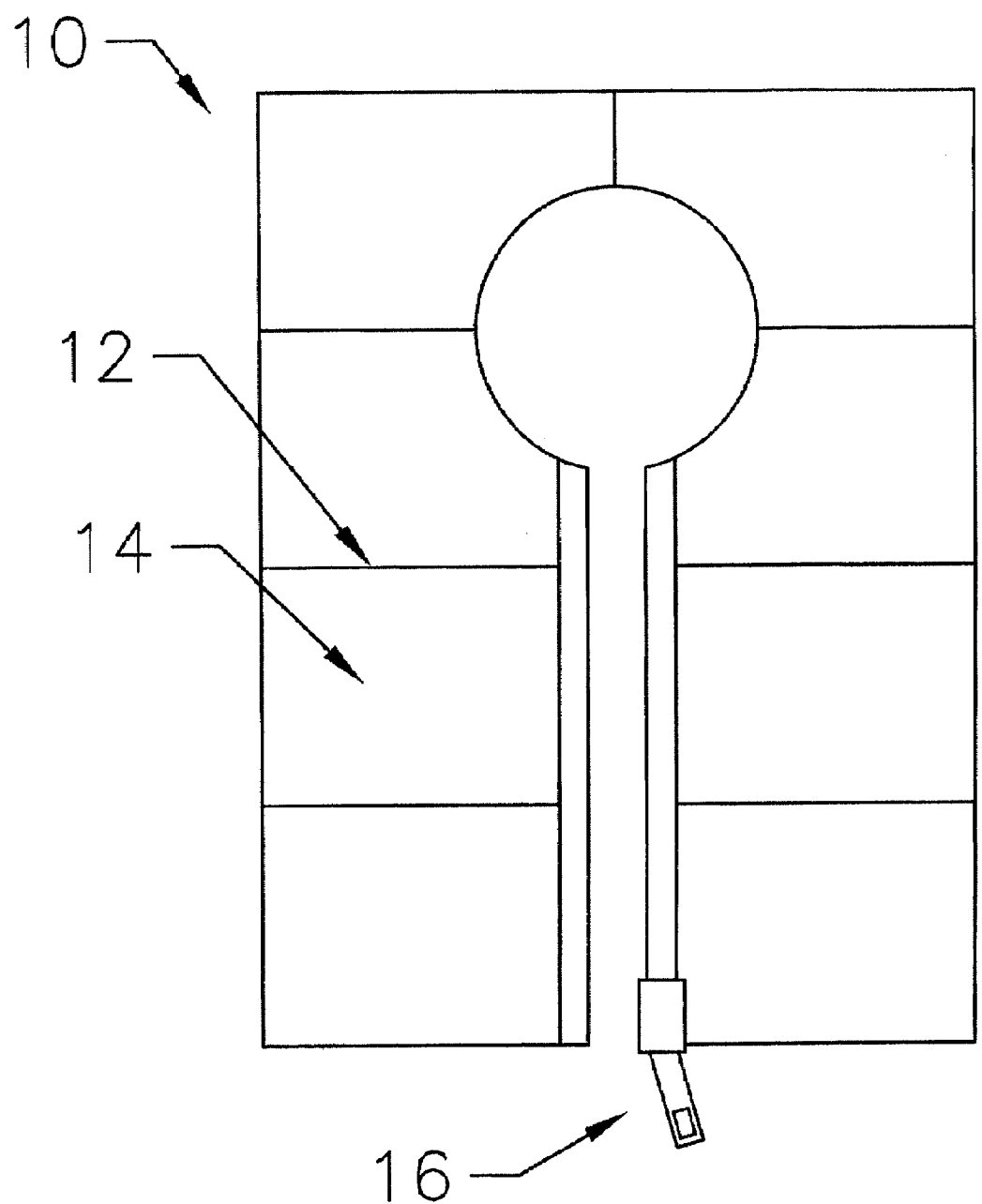
FIG. 1 shows an embodiment of a life vest embodiment of the invention, which is continuously inflated.

FIG. 1 shows one embodiment of the present invention. Here a life vest 10 is made using a film that is translucent to ultraviolet light. A good example of such a film is polyvinylidene fluoride. PVDF is distinctive among polymers in that rather than degrading from ultraviolet light it actually gets stronger by cross-linking. An oriented PVDF film is a good transmitter of ultraviolet (UV) light and can have a transmittance as high as 85% -90%.

Other useful materials include Ecdel from Eastman Chemical Company of Tennessee, TPX of Mitsui Plastic's Inc. of Japan, Teflon of DuPont Engineering Polymers, and Tenite of Eastman Chemical Company of Tennessee. Another suitable material would be a light stabilized polyamide based material. Such a light stabilized material is available from Allied Signal Incorporated of Morristown, N.J.

The practitioner in the art can find many useful references to assist in the choice of an appropriate material or fabric. For example, a material that will transmit visible and UV light but block infrared is taught in Allingham, et al. Mutzhas and Longstaff each teach appropriate materials for transmitting UV-A (lower frequency ultra-violet) and violet (visible). The following discussion of some of these material choices is liberally taken from them.

Polymers passing solar radiation, yet blocking infra-red radiation, can begin with a matrix of polyethylene or a copolymer in which polyethylene predominates, containing a sufficient quantity of a metaphosphate of a metal chosen from among group 1 to 3 of the periodic table. The addition of certain phosphates, and especially metaphosphates does not perceptibly impair the transmission of solar radiation, but changes in a very pronounced manner the transmission of infra-red radiation.

If the polyethylene or polyethylene copolymers have a finely dispersed phosphate ion (such as $PO_4^{-3}$) it will have a strong absorption in the IR region, while being substantially transparent in the visible range. The phosphates used are typically insoluble forms of sodium- potassium- calcium- or aluminum-metaphosphate. The quantity of these incorporated in the polymeric matrix may be varied between 1 and 20 percent by weight, the preferred range being 3 to 10 percent by weight. The preferred polyethylene is low density polyethylene or copolymers of ethylene with vinyl acetate. The insoluble forms of the above metaphosphates can be blended with a granulate of polyethylene by standard industrial processes, such as milling or double screw extrusion. The material can be blow-extruded and the resulting films have good mechanical strength. Experiments have shown that films of low density polyethylene containing from 5 to 10 percent by weight of sodium metaphosphate, or of potassium metaphosphate have good mechanical properties; they are substantially transparent to solar radiation, yet absorb at least 80 percent of infrared radiation.

Metaphosphates, or polymethaphosphates of aluminum, calcium, barium, etc. may also be suitable.

For the Tan-Thru™ embodiment the plastics material, which preferable is a thermo-plastic material or acrylic resin in the form of either a thin film or woven or knitted material, should exhibit the property of being transparent to long wave UV-A radiation of wavelengths between 320 and 400 nm and to visible light in the range between 400 and 450 nm which are those particularly associated with immediate pigment tanning. In addition, the visible light associated within the range 450-700 nm and a major portion of the IR wavelengths greater than 700 nm are absorbed.

Suitable materials are resins of vinyl chloride, polyolefins such as polyethylene and polypropylene, or acrylic resins such as polymethyl-methacrylate. The vinyl chloride resins referred to are homopolymers or copolymers of vinyl chloride and such resins may, in addition, contain plasticizers preferably of phathallate esters. Copolymers such as polyethylene/vinyl acetate and butadiene/styrene would also suffice. A preferred material is a plasticized polyvinyl chloride film of thickness between 100 and 300 microns, for example, 175 microns, and this may be a single film or a laminate formed with a reinforcing nylon or polyester net to give greater physical strength.

Whichever of the resins is used, it should not have a significant absorption, i.e., greater than 30%, of radiation of wavelengths between 310 and 450 nm. The resin should also be light-stable and non-volatile at the relatively high temperatures used in extrusion or callendering (i.e. about 150°-200° C.). Because these resins are transparent to substantially all of the available energy in the UV-A and UV-B wavelengths and most of the visible and IR spectrum, additional agents described below need to be added to the formulations to selectively filter the wave bands of light previously mentioned in order to achieve the desired effects.

As an alternative to rigid or plasticized thermoplastic film, a woven or knitted fabric preferably of nylon or polyester filaments may be used. A suitable support material is the polyester polyethylene terephthalate. Care must be taken to ensure that the particular cross-section of the fiber, the number of fibers per element and the orientation of the fiber in the woven or knitted fabric does not cause excessive light reflection or defraction. One example is ICI polyester.

A second fabric alternative to rigid film would be TietexR™ 18 gauge warp-knitted polyester. This particular fabric has highly organized linear orientated fibers which minimizes light defraction and encourages high general light transmission.

Because these polyesters have a high UV-B absorbing capacity in their own right, i.e. without additional UV absorbing agents, only those agents imparting visible and IR absorption need be added to create an ideal sunscreen.

The agent used typically in the rigid or plasticized film to achieve UV-B leakage in the range of 310-320 nm is ethylhexyl-p-methoxycinnamate at a weight concentration of 0.05%, when the film thickness is between 100-300 microns. For the same film, pigments such as Microlith Violet B-K, Cromoptal Blue A3R (Ciba-Geigy) and PV Carmine HF4C (Hoescht) at a concentration of 0.1% w/w provide ideal visible light absorption as well as imparting attractive coloration, and a heat sink comprising thermal black (finely divided carbon black) at a concentration of for example, 0.5% w/w, to absorb IR radiation. Film compounded from plasticized PVC and containing the above ingredients serves to transmit 20% UV-B in the wavelength range 310-320 nm, but excludes substantially all UV-B in the range 290-310 nm.

Similar levels of UV-B irradiance in the range 310-320 nm would be achieved by deployment of the previously described fiber fabrics, suitably surface printed or dyed with disperse dyes such as Dispersol Red B2-B at 2.25% w/w concentration. Infra-red may be absorbed by carbon black as previously described or reflected by titanium dioxide.

The life vest embodiment is made by having vertical separating walls 12, which break the vest into chambers 14. Each chamber 14 is filled with ultraviolet transmitting gas such as carbon dioxide or air or nitrogen among many others.

A molded plastic zipper 16 is used to secure the vest to the subject. Other methods of securement could be used as well. Straps to go around the back or crotch straps 200 (see FIG. 14) would also be acceptable. They preferably would be made of an oriented PVDF or other UV transmissive materials.

The vest in FIG. 1 shows one embodiment for an over-the-neck type of life jacket. The same idea of the invention could easily be applied to a traditional vest type that goes all around the back without departing from the spirit of the invention. This is shown is later figures.

Figure 2:
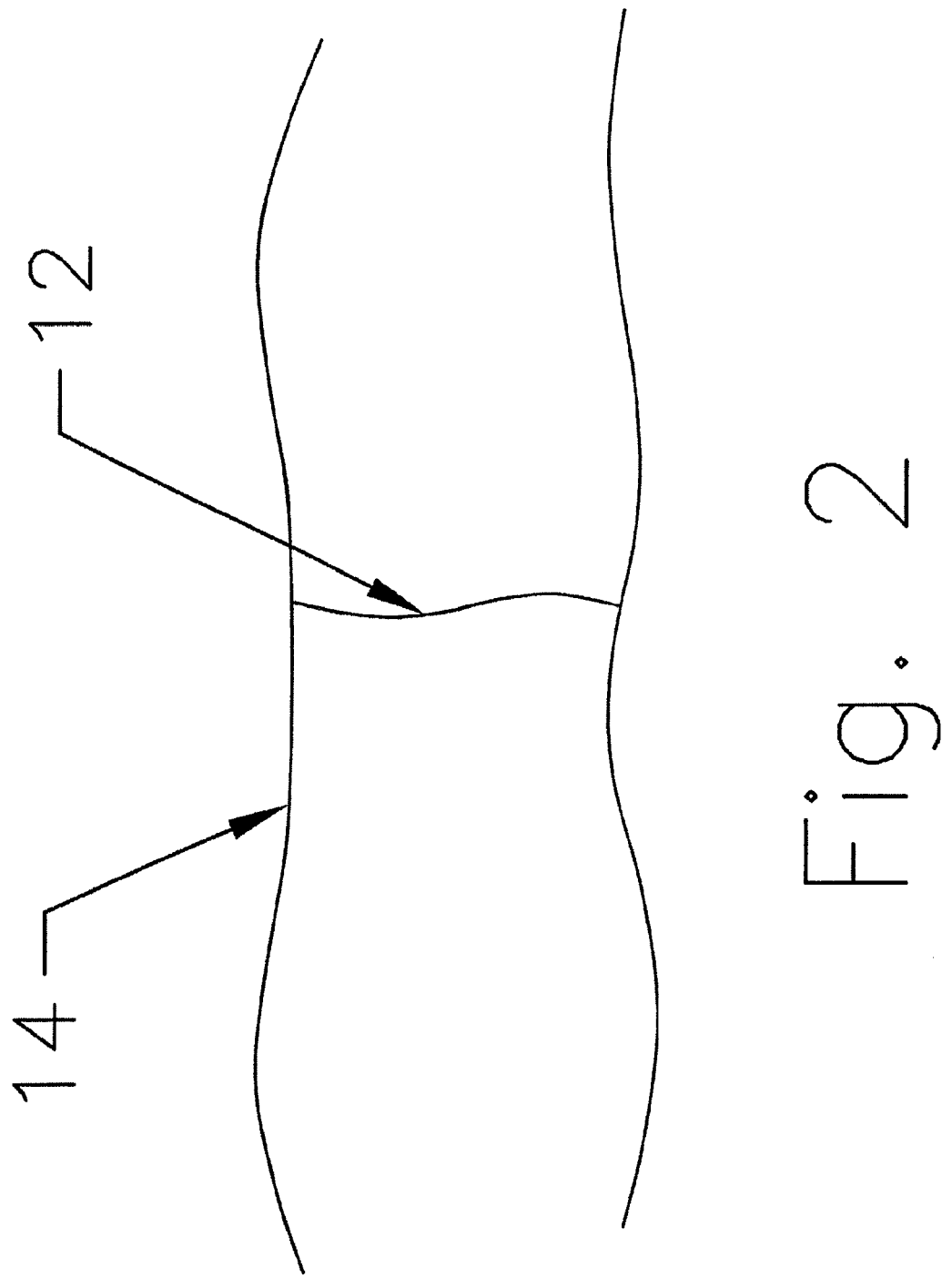
FIG. 2 shows the side view of the continuously inflated life vest embodiment.

FIG. 2 shows a side view of the cells of the invention as shown in FIG. 1. Bulkhead walls 12 again are separating the vest and the chambers 14 from each other which are each filled with the inert gas.

Figure 3:
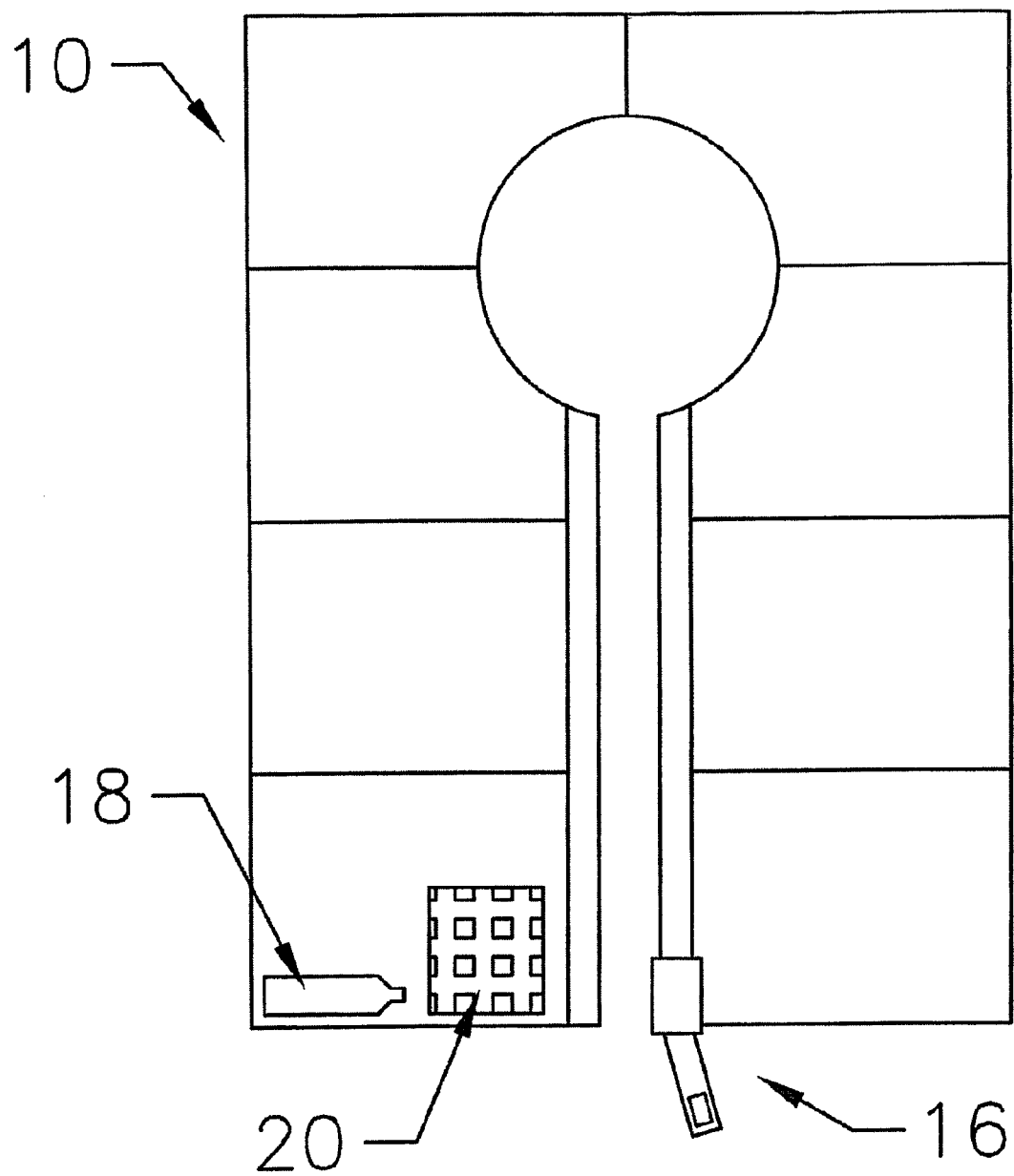
FIG. 3 shows a plan view of the acutely inflating life vest embodiment of the invention.

FIG. 3 shows an embodiment of the present invention that inflates only in response to water immersion. This "acute" embodiment uses a compressed carbon dioxide reservoir 18, which is triggered by the water sensor 20 to release the carbon dioxide into the vest to inflate it. Other compressed gases could be used as well.

This vest would be very comfortable and lightweight for subjects and yet would inflate instantly upon immersion in water. Even if the material is not 100% transmissive to the ultraviolet light, one can match the transmission by using the appropriate degree of sunblock on the exposed limbs. For example, one might use a 4 or 6 level sunblock on the arms to avoid having any contrasting tans.

Figure 4:
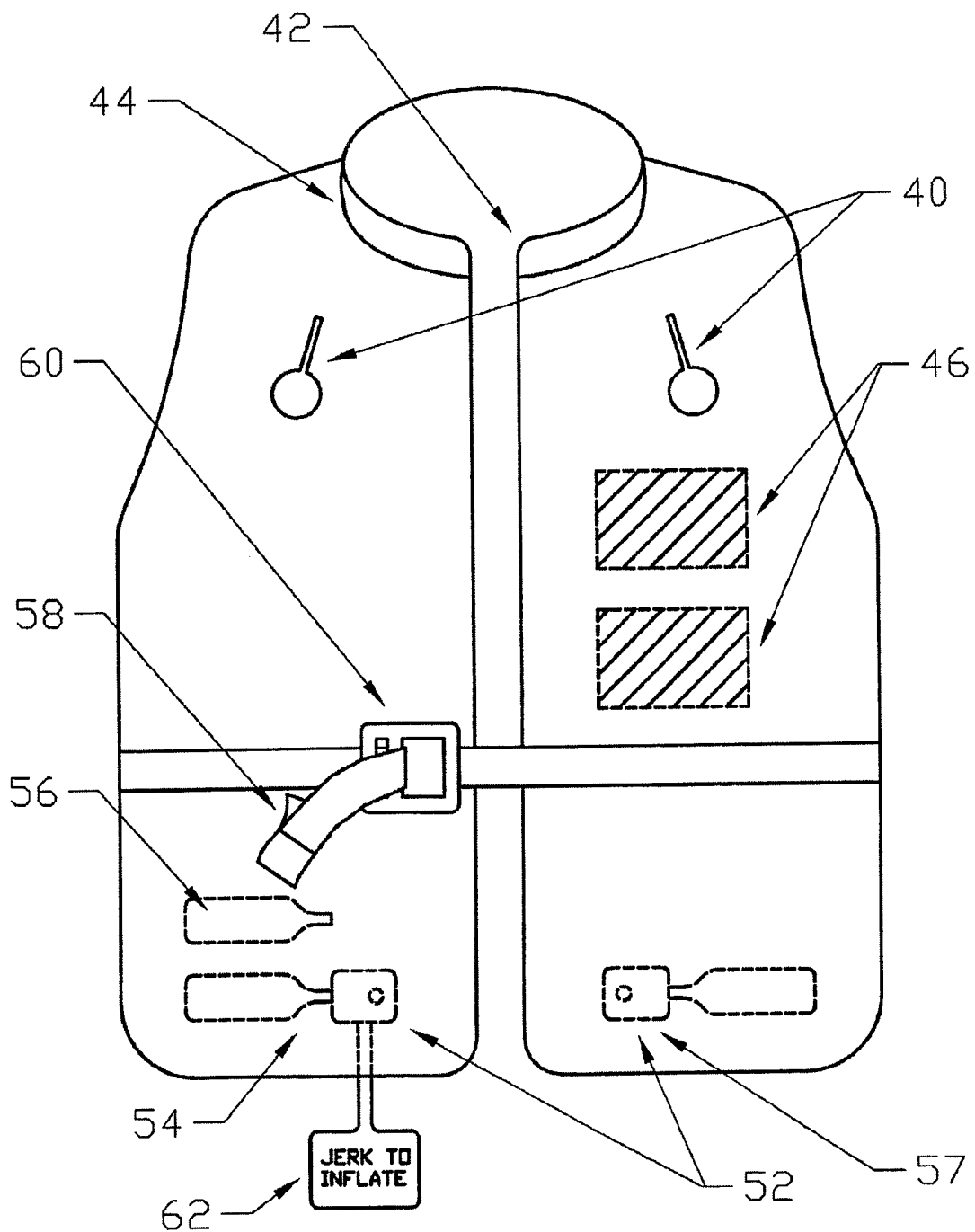
FIG. 4 shows details of the emergency inflating version.

FIG. 4 shows a more detailed version of the inflatable embodiment of the invention. The vest has manual inflation straws 40 as well as emergency inflation handle 62. The emergency inflation handles 62 allows the gas from the CO2 cartridge 54 to immediately fill the vest. A spare CO2 cartridge 56 can also be incorporated in the vest. Item 57 is an automatic inflation means. This system works by either sensing the water electrically or through a fast chemical solution to allow the CO2 to be injected into the vest. The closure 60 needs to be strong enough to hold 1600 newtons of force (360 lb.) alone or through the combined strength of multiple closures.

Passive intrinsic flotation means 46 are an alternative also included in the vest. These can be made of light transmissive foam. The vest includes very reliable securement means to pull the two sides of the vest across the users chest 60 along with a retainer 58 for each adjustable closure 60 to prevent it from being easily removed. All corners 42 are rounded to prevent irritation or cutting of the user and edges 44 are heat sealed to prevent leakage.

Figure 5:
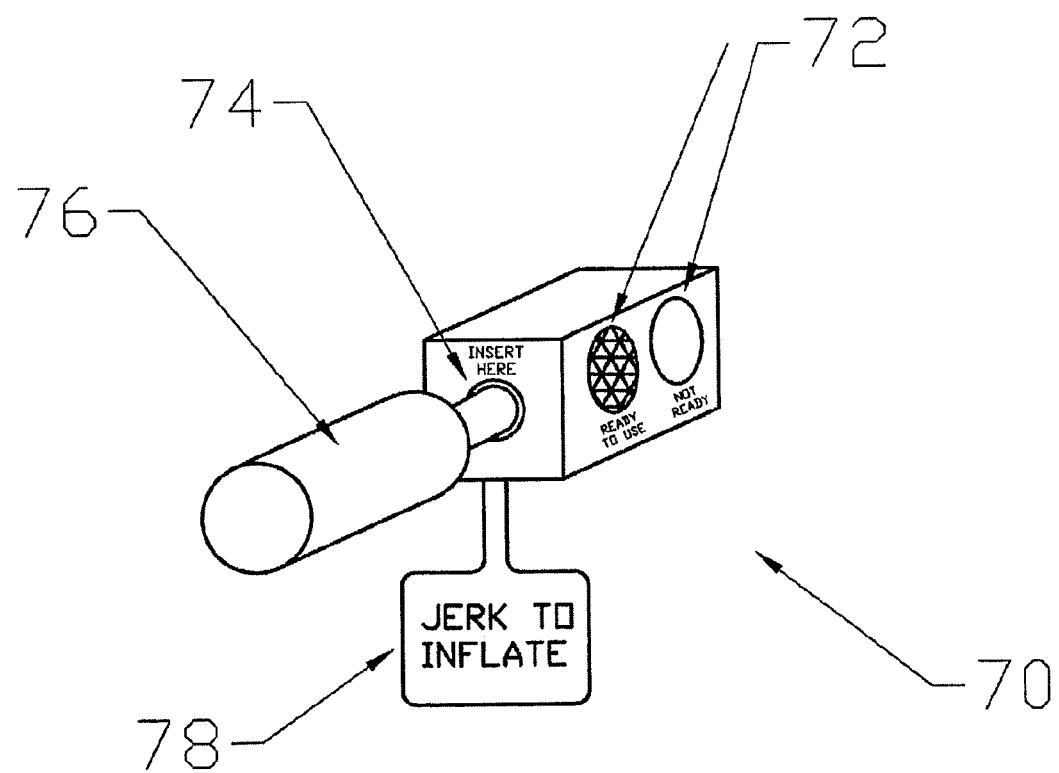
FIG. 5 shows the details of the rapid inflation mechanism.

FIG. 5 shows the details of the rapid $CO_2$ inflator. The system 70 has an indicator 72 to indicate whether the system is ready to use or not. The 12-gram $CO_2$ cartridge 76 is inserted into an insert 74. The handle 78 is jerked to instantly inflate.

Figure 6:
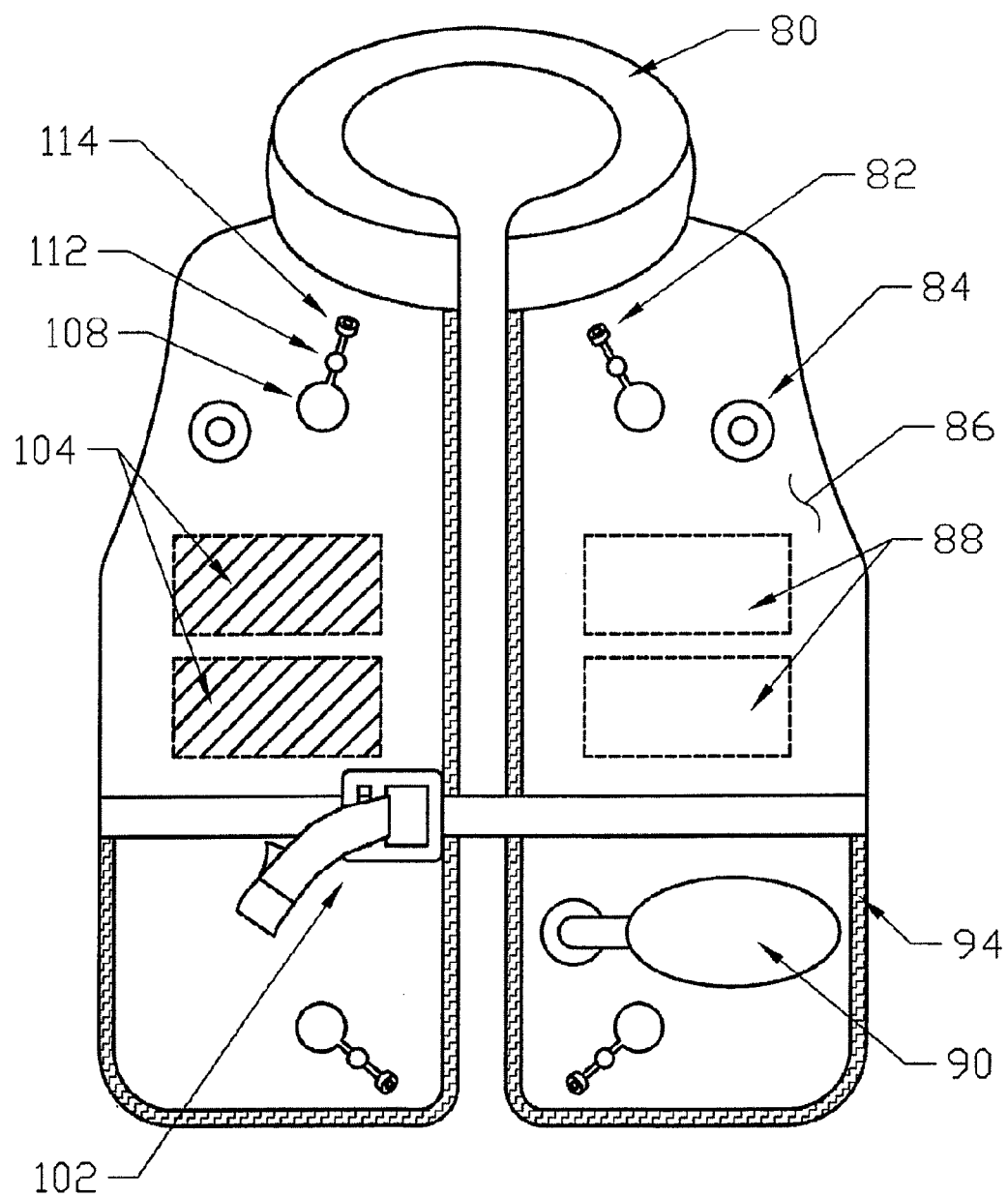
FIG. 6 shows details of the manually inflating hybrid version.

FIG. 6 shows more details of a deluxe embodiment of the invention. It begins with an inflated collar 80 to help right the wearer in the water. The passive inflation mechanism 82 is shown in four locations: the top and bottom of the vest and the left and right sides. Each mechanism 82 has a non-toxic mouthpiece 114 and a deflation squeeze bulb 112. Each is bonded to the vest with a transparent collar 108.

The vest may have passive flotation elements, which are merely a sealed gas such as the pockets 88 or of transmissive foam such as those in pockets 104. An integral pump 90 can be used if someone would rather squeeze with their hands then to blow air into the device.

Pressure release valve 84 found on each side of the vest is to release excessive pressure from a $CO_2$ malfunction, excessive manual inflation followed by high temperature, or someone jumping on the vest. This would allow enough air to leak out to prevent damage to the vest. The seams 94 are sewn to meet the Class 300 lockstitch level to meet federal standard 751.

Figure 7:
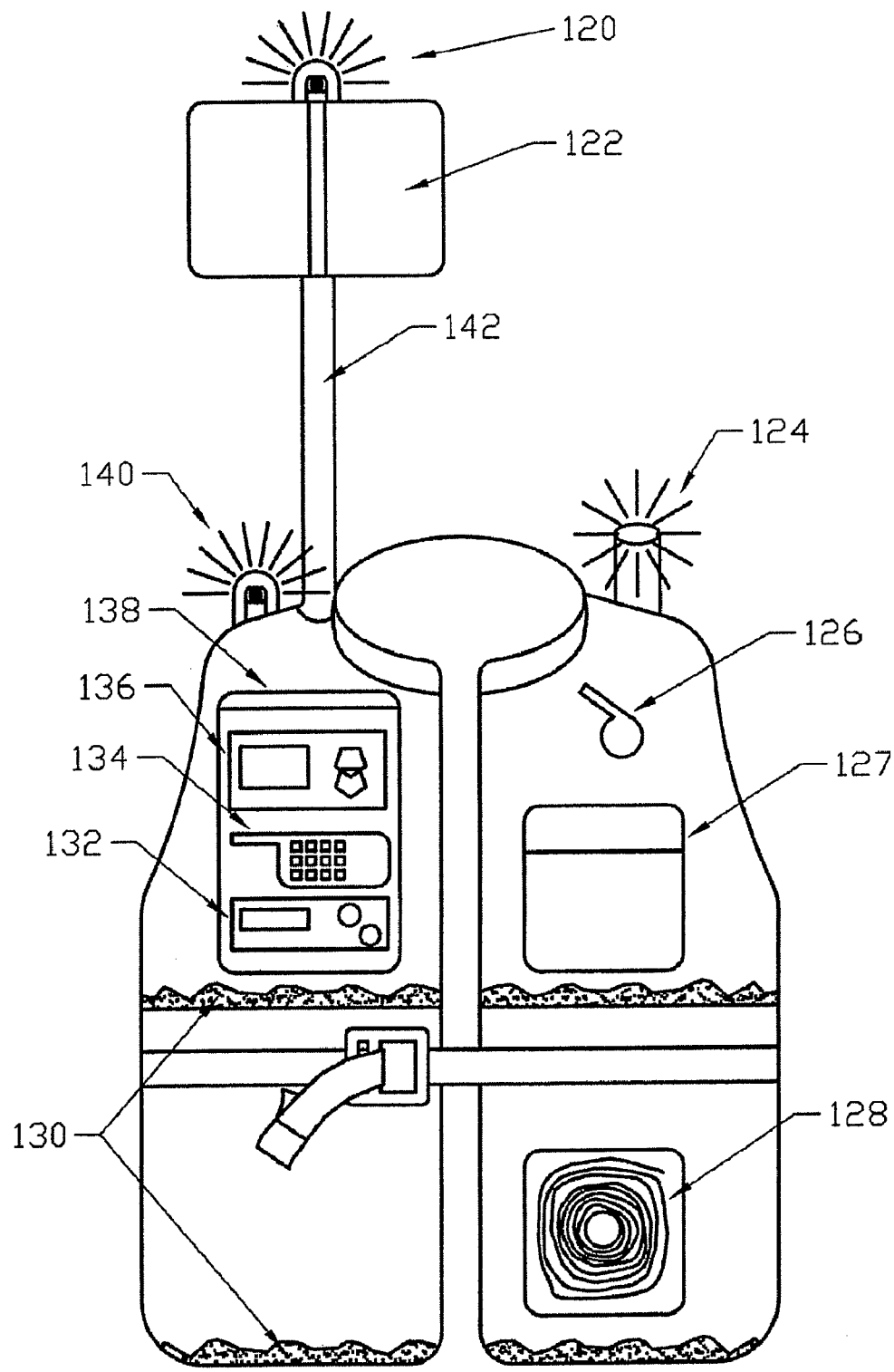
FIG. 7 shows details of a full emergency system with whistle and flashers.

FIG. 7 gives details of the embodiment of the invention optimized to enhance the rescue of the wearer. The automatic inflation causes the mast 142 to inflate which positions flashing light 120 above the head of the wearer. This also positions metallized flat surface 122 above the head of the wearer to better reflect radar. Incorporated in the light 122 could also be an ELT beacon or automatically operated cell phone to generate a distress call. Conventional strobe light 124 or glowing light 140 are shown as alternative embodiments to be attached to the main part of the vest. Whistle 126 is also available for the wearer's use. Pockets 127 can be used by the wearer to store emergency supplies or keys. Pocket 128 holds a long fluorescent colored ribbon to further aid in the rescue of the wearer. A first aid kit 136 could be included as well as cell phone 134 and patch repair kit 132.

The automatic inflation as well as the permanently inflated PFD chambers have integral fluid which is not hard in the presence of $CO_2$ but hardens very quickly in the presence of oxygen or nitrogen. Thus if any leak were detected these would be self-sealing. This would be especially true along the stitch cracks of the stitching 130. This self-healing fluid would not work with breathing inflation as the oxygen and nitrogen from the breath would initiate the sealing process.

Figure 8:
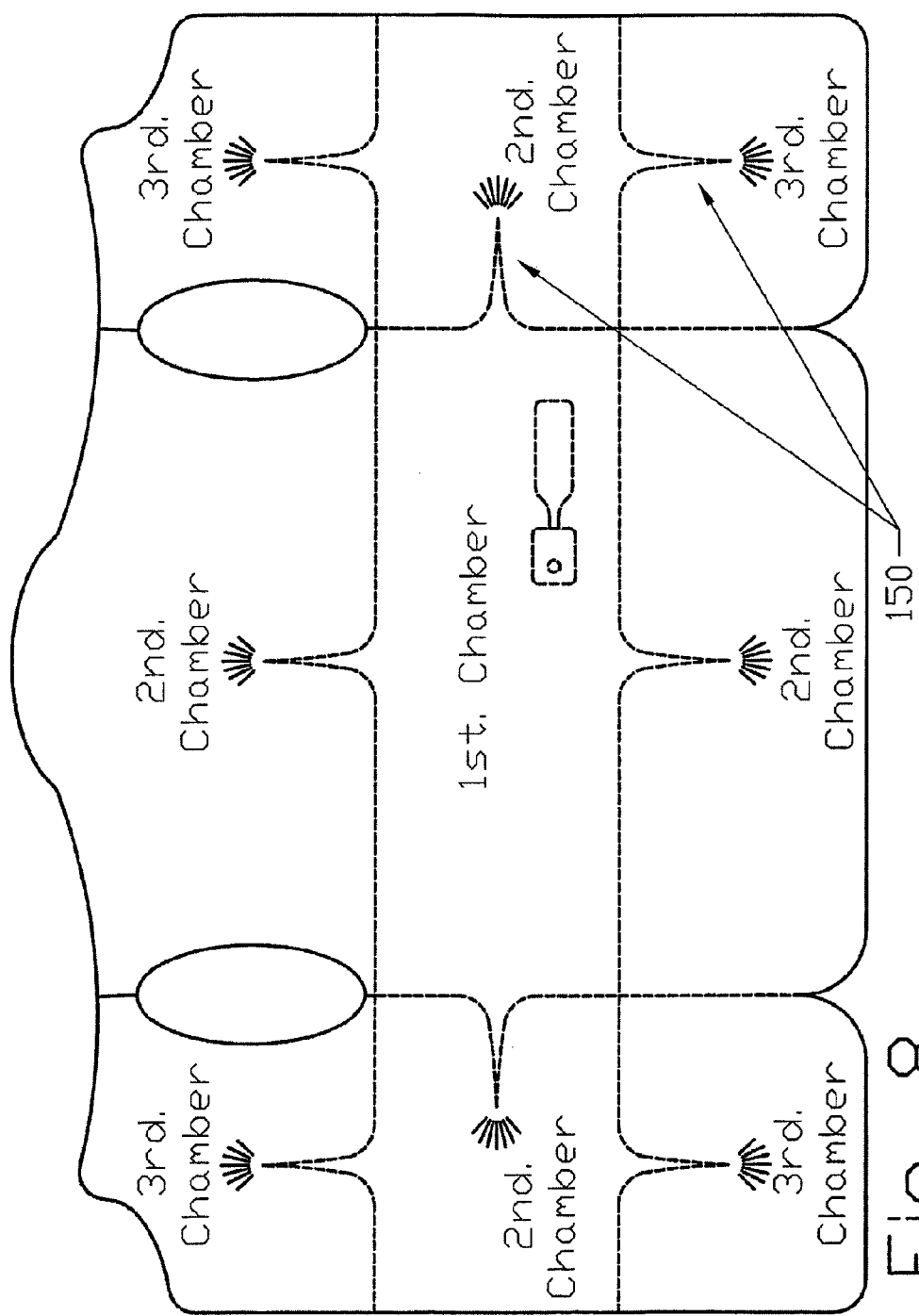
FIG. 8 shows system with multiple chambers with protective valves.

FIG. 8 shows means of allowing a single path of inflation means or pressurized gas means to inflate the vest and yet maintain integrity of the multiple chambers. With this design there is a bi-leaflet reed valve 150 between a pressurized supply chamber and the receiving chamber. This allows the flow of the gas from the pressurized source to all chambers. However, if one of the chambers develops a leak it will not discharge all of the chambers. For example if the primary chamber 1 develops a leak it will only discharge itself.

If, in a worse case situation, one of the third level chambers were to be punctured and completely deflate, it would deflate itself as well as the second level chamber that fed it and the first level chamber. However, this is only 3 of the 9 chambers lost due to the severe deflation on the one chamber and is much preferable to having the whole system deflated.

In the alternative a valve system could go by hose from the pressure and gas source to each one of the individual chambers. This would ensure that the deflation of no chamber could interfere with its neighbors. However, this adds expense and weight and makes transmissibility of visible and ultraviolet light more problematical.

Figure 9:
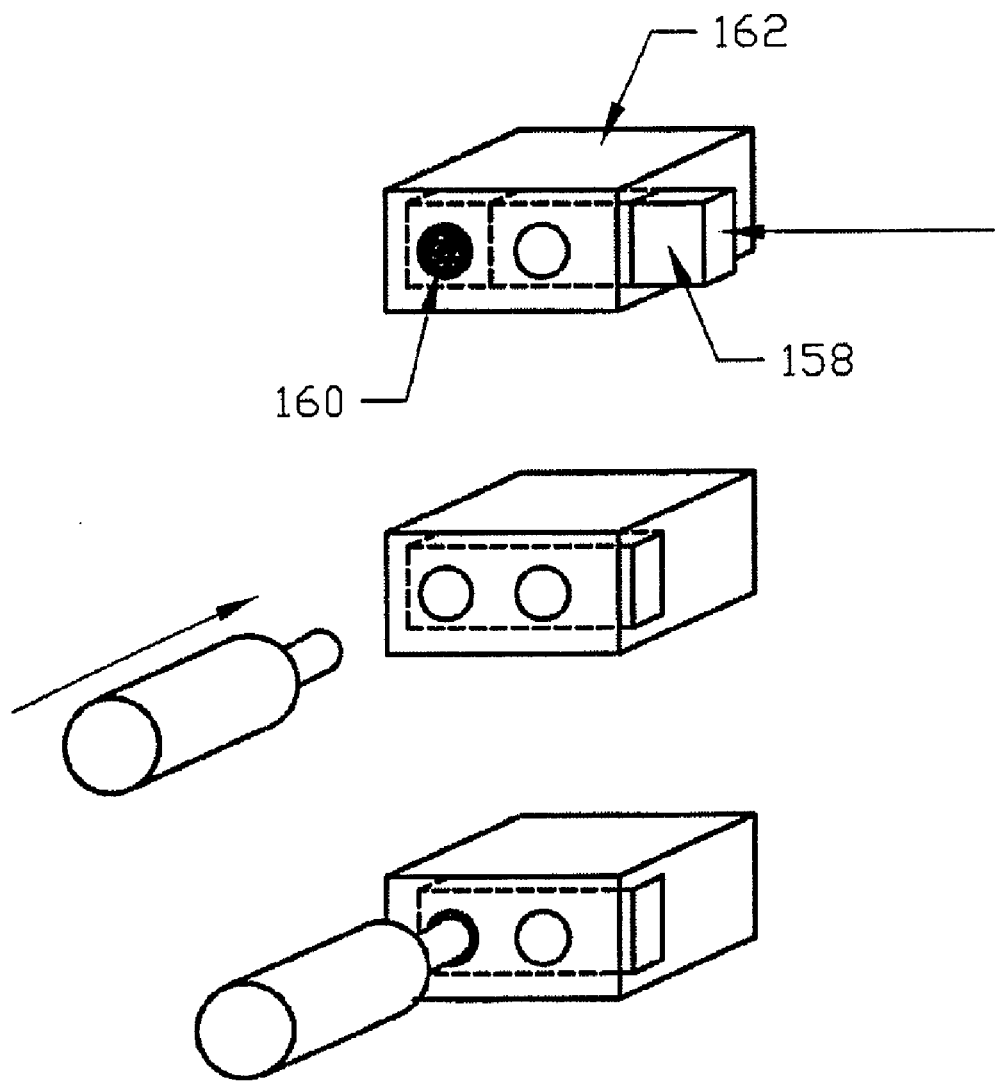
FIG. 9 shows the foolproof mechanism for gas cylinder installation.

FIG. 9 shows the detail of the fail-safe mechanism for the water sensitive element. If the water sensitive element 158 is not fully inserted into the sensor mechanism 162 then the hole 160 will not be able to allow the insertion of the $CO_2$ cartridge.

Figure 10:
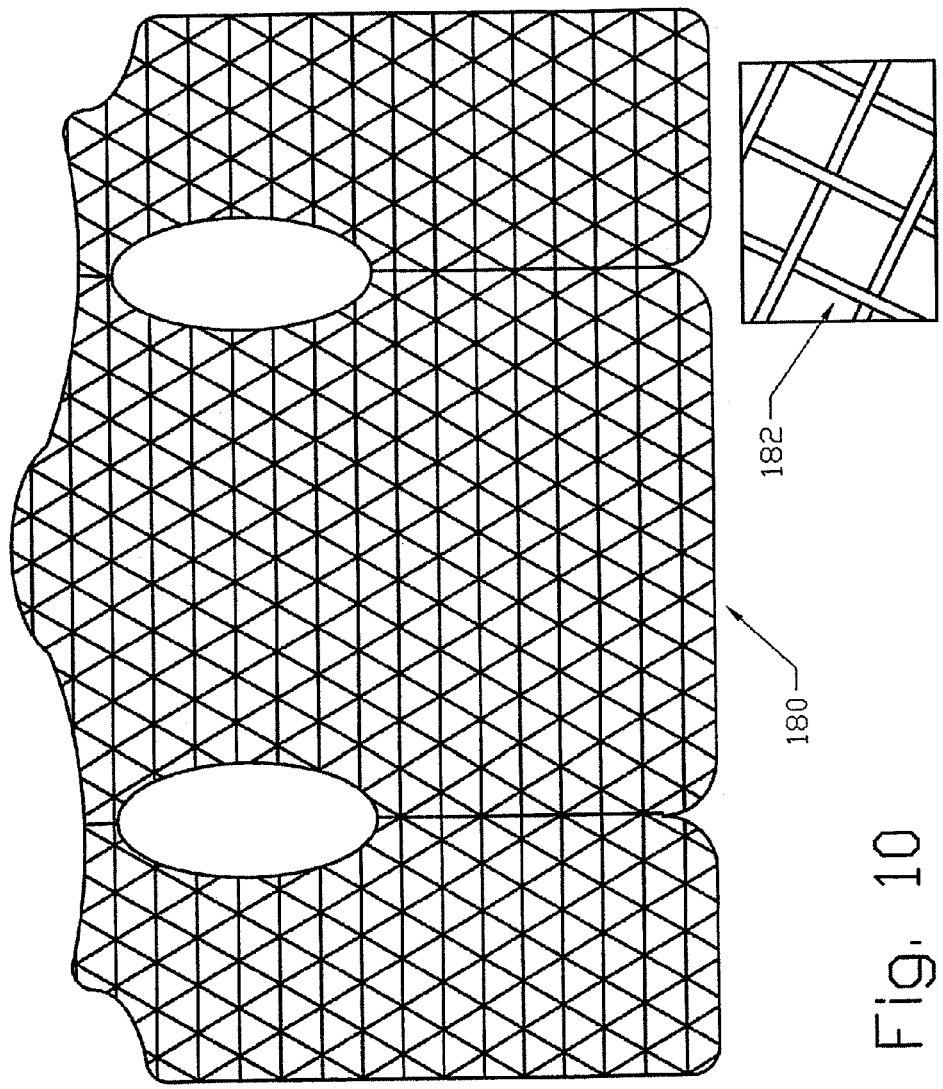
FIG. 10 shows the embodiment of an integral coarse weave fabric to minimize the stickiness of the inside of the clothing embodiments.

FIG. 10 shows the detail of a rough mesh backing to improve wearer comfort. The back of the vest 180 is covered with a very coarse mesh 182 to allow for some air circulation and to decrease the uncomfortable stickiness of the vest.

Figure 11:
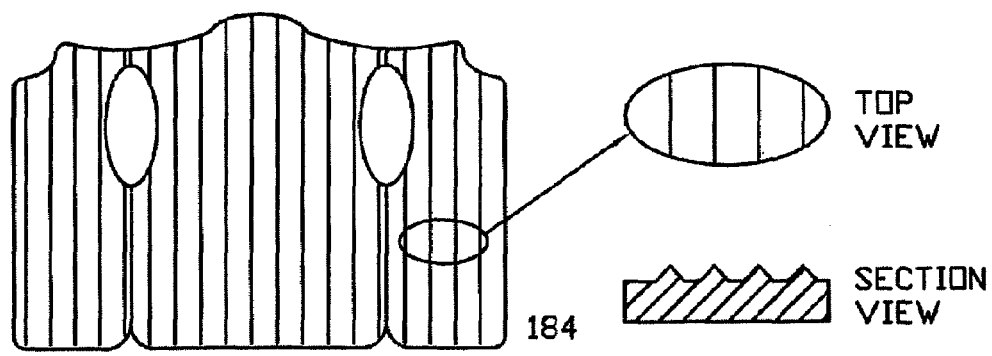
FIG. 11 shows textural solutions to the stickiness problem.
Figure 11:
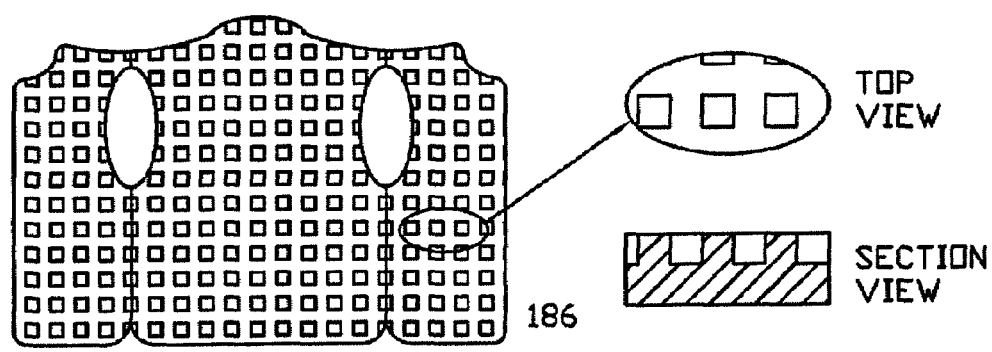
Figure 11:
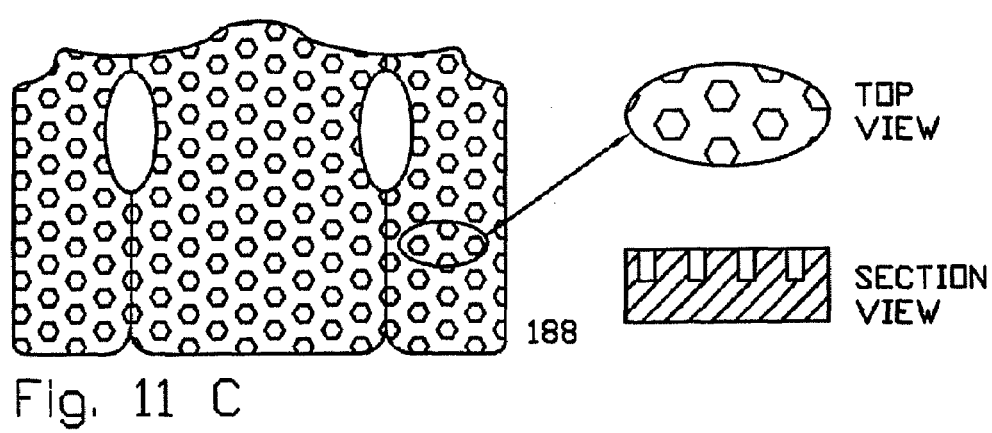

FIGS. 11*a*, *b*, and *c* show alternative backings to reduce the discomfort from the plastic adhering to the skin. In FIG. 11*a*, rib design 184 has a structure to keep the backside of the vest off of the skin. This allows some circulation of the air from top to bottom through the vest. In FIG. 11*b*, crosshatched design 186 reduces the area of the vest that is in direct contact with the skin but does not allow any airflow. In FIG. 11*c*, dimpled design 188 is the preferred approach as it allows airflow in both directions under the vest.

Figure 12:
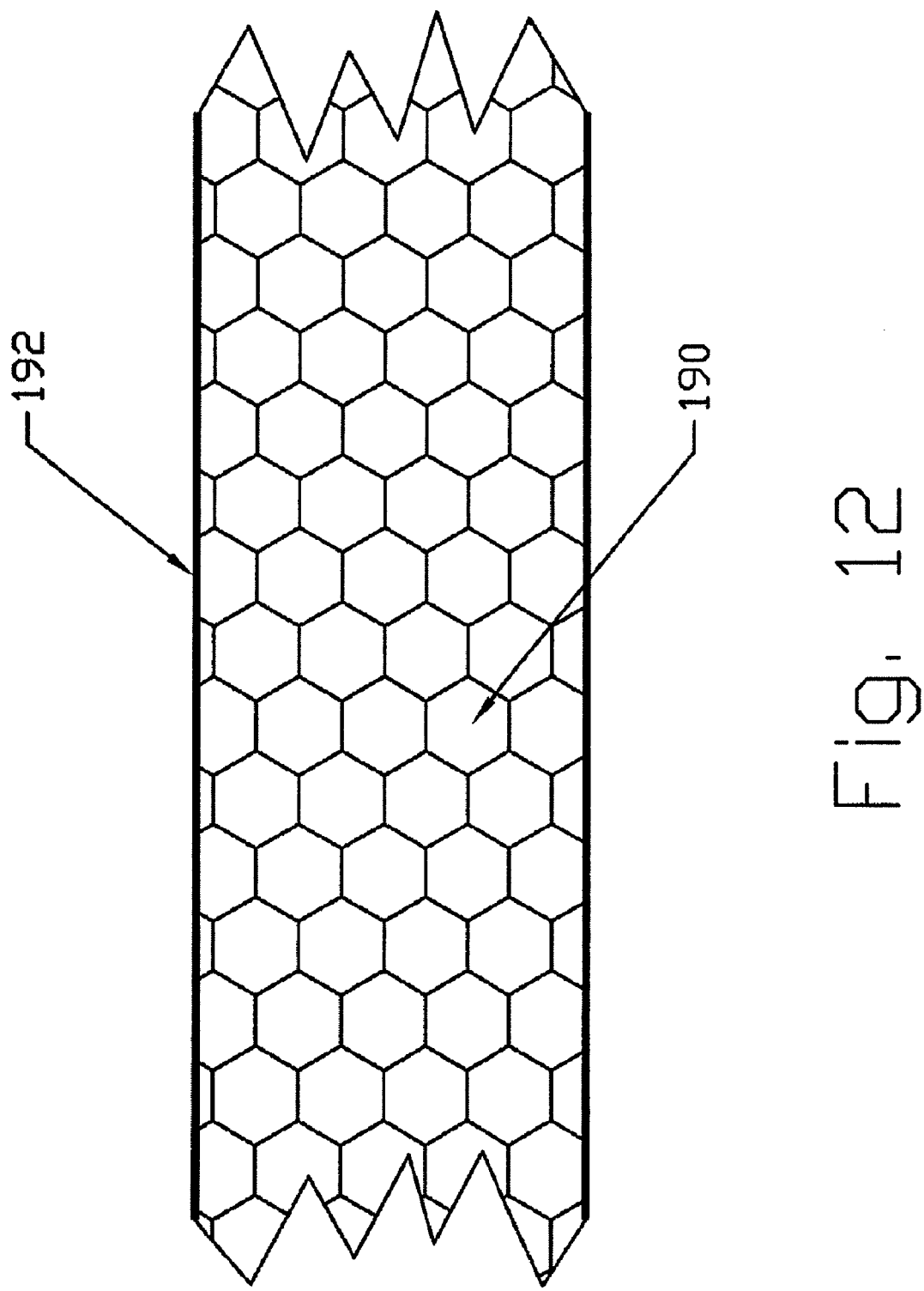
FIG. 12 shows the foam used in one embodiment of the invention.

FIG. 12 shows the closed valve cell foam embodiment of the invention. In this embodiment the chambers are made of closed cell foam 190 which is protected by transparent film 192.

Transparent foam is very difficult to make because of the Snell's law causing multiple pathways for the light as it goes in and out of each cell. However, the foam can be made translucent to allow the passage of ultraviolet light. A representative translucent foam material is high clarity polypropylene combined with endothermic buoying agents which is available from Coral Foam Company located at www.Coralfoam.com.

Also the NuSil Technology Company of Carpenteria, Calif. has a product R1-2354 which is a high strength RTV silicon foam which when catalyzed yields a medium density flame retardant silicone foam which is flexible and translucent.

These foams, while they are not transparent enough to, say, read a newspaper through, will allow, with some distortion, the basic images of a bathing suit to come through and thus achieve some of the vanity and appearance goals of the invention.

Figure 13:
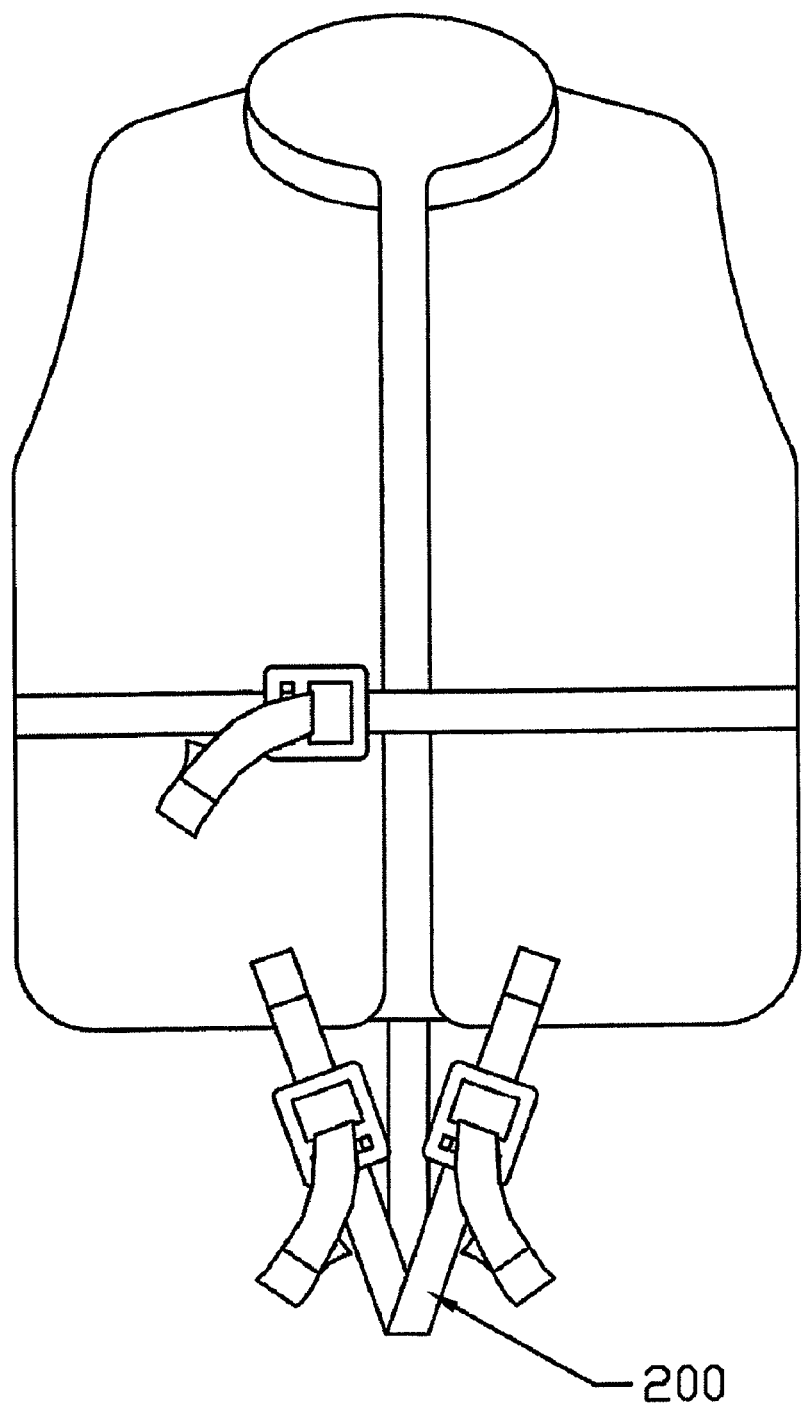
FIG. 13 shows the use of crotch straps for further securing the life vest to the body.

FIG. 13 shows the life vest embodiment of the invention with crotch straps. The importance of these straps lies in the Coast Guard classification of life vests for slow speed usage. In order to have a vest approved for higher speed usage, it must be very securely attached to the body. The crotch strap would allow the life vest of the instant invention to be used with, say, jet skis.

FIG. 14 shows an embodiment of the invention with the gas holding pockets being distinct from the outer fabric. This is because an optimal material for gas impermeability may not be optimal for abrasion resistance. Thus one could select a transparent polyvinyl (moderate abrasion resistance) for the internal gas pouches but use a high abrasion resistant material for the outer layers.

For a Tan-Thru™ life vest one would like to transmit UV-A for the melanization (skin tanning) properties but to limit the carcinogenic UV-B. The visible light is blocked for reasons of modesty and consumer choice. For the UV-A infrared radiation, we have two choices which can really correspond to two products, hence labeled optional.

For the Fast-Tan™ life vest, the UV-B would also be passed as the UV-B is a strong promoter of melanization.

For the See-Thru™ life vest, the visible light is passed but both of the UV wavelengths are blocked. The infrared treatment is optional as discussed above. For the See & Tan-Thru™ life vest both visible and UV-A light are transmitted but the UV-B is blocked.

The Greenhouse™ snow-ski vest (alternatively a coat with full length sleeves) would transmit UV-A. Visible light is blocked to allow for the more modest consumer. The UV-B passage is optional. Blocking this reduces ultraviolet damage to light sensitive clothing beneath the vest. Gas filling is optional as it presents more insulation but also more bulk. Note that a single layer of UV-A passing material can warm the user.

The Show-Me™ ski vest or jacket passes visible light to allow the wearer to reveal clothing or physique beneath. The UV-A passage is optional depending on the amount of warming desired. No gas filler is used for this embodiment.

FIG. 15 shows the Air-Bag™ snow ski pants 230 which are gas filled. They offer light weight warmth and cushioning for falls. They protect the hips from falls as air is a very good shock absorber. They would pass visible light to prevent apparent bulk. Other light wavelength passage choices are optional. They are either worn over or under shorts 240 or long underwear. The pants are filled permanently with multiple chambers such as shown in FIG. 14. Alternatively, each pant sleeve is one chamber with tension pylons spaced every 1.5 cm to prevent bulging.

Figure 16A:
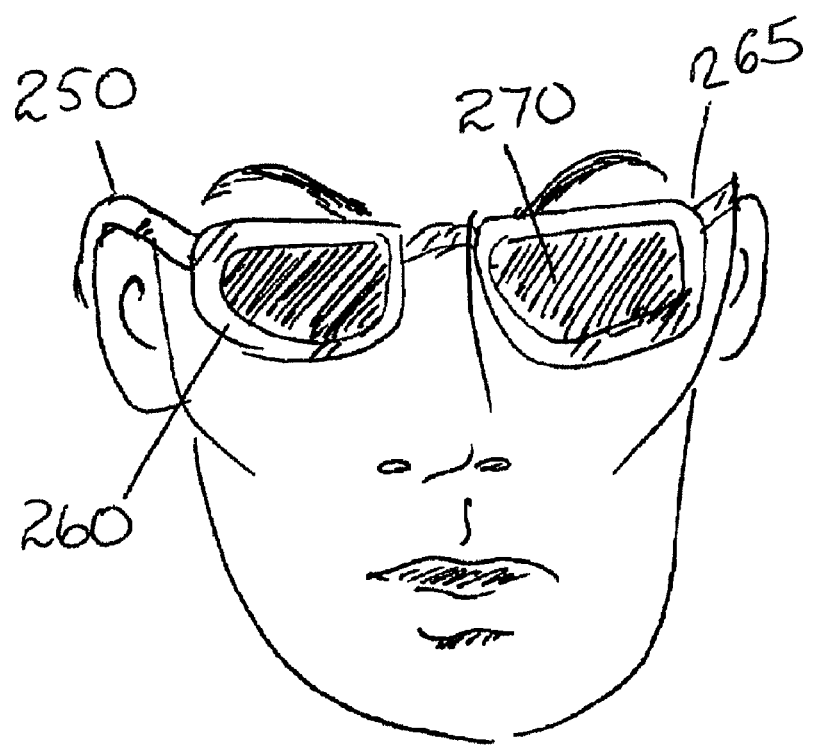
FIG. 16A shows the tan-thru sunglasses embodiment.

FIG. 16A shows the tan-through sun glasses embodiment of the invention. Here the bows 250 are made of a fully or partially UV passing polymer. This polymer is preferably also transparent to visible light. Alternatively, the bow is only transparent to UV light. This allows tanning to occur under the bow lines so that the unsightly tan lines do not develop. The frames 260 are preferably opaque to UV light to give maximum protection to the eyes. Alternatively, the frame is transparent to UV light at the brow line to eliminate that possible tan line. The lens 270 is made of conventional material. Bow thickness may vary. For example, the thickness of the bows 250 may be tapered and generally thicker nearer the frame. So configured, the generally thinner areas of the bows 250 may pass generally more UV light than the thicker sections of the bows 250. In other examples, the same amount of UV light may be passed in both the thick and thin sections.

Alternatively, there is a minimal frame as the bows connect either directly to the lenses or through a hinge mechanism 265.

Figure 16B:
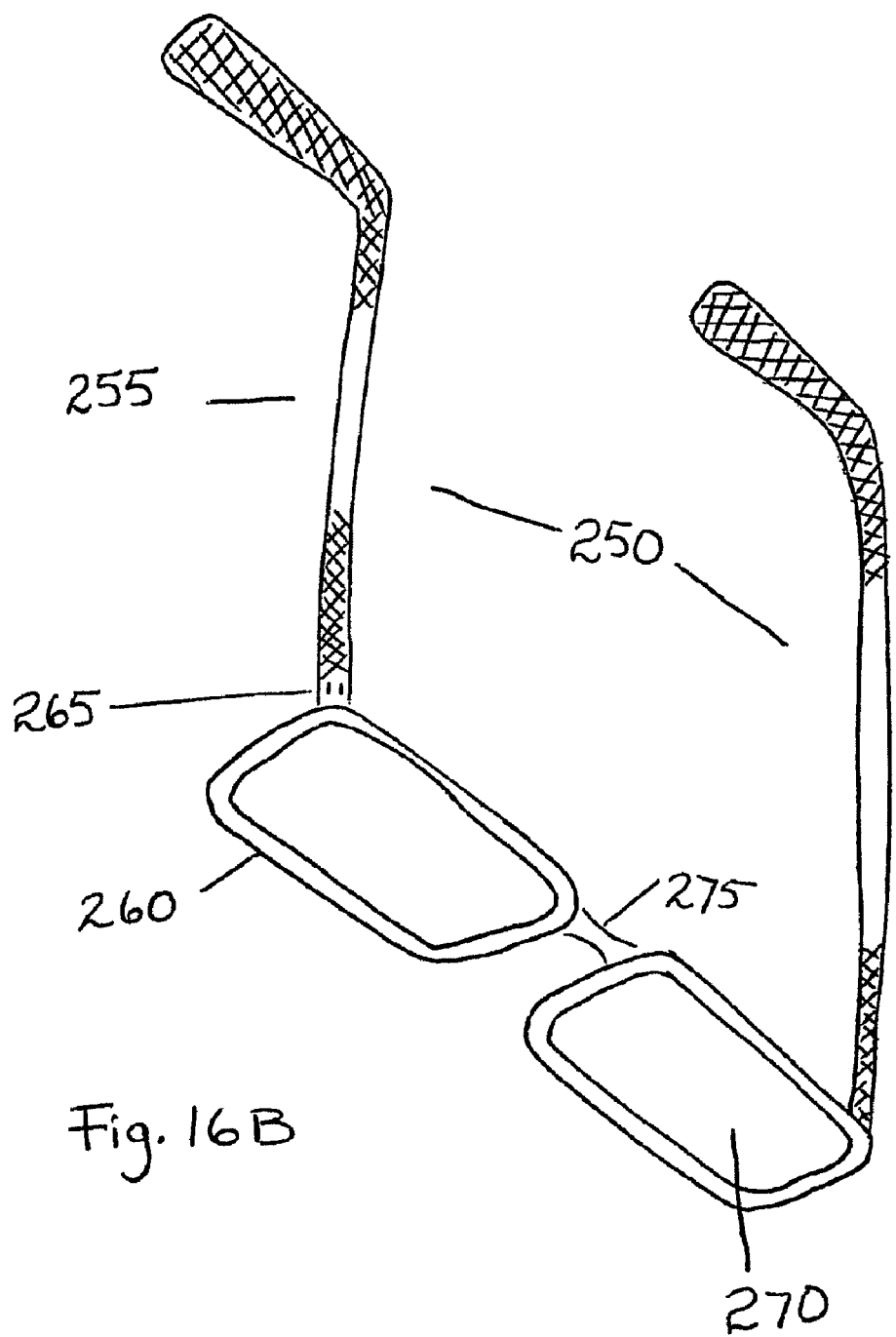
FIG. 16B shows the tan-thru eye glasses embodiment.

FIG. 16B shows the vision-improving eyeglass embodiment of this invention. Bows 250 secure the eyeglasses to the wearer's ear and attach to a hinge mechanism 265. Alternatively the hinge mechanism is replaced by a partially flexible connection. The hinge mechanism then connects to the frame 260 which connects to corrective lens 270. The two frames are connected by a nose bridge 275. Alternatively, the hinge mechanism 265 and the nose bridge 275 attaches directly to the corrective lens 270 and the frame 260 is a de minimus attachment point for the hinge and nose bridge.

The bow 250 is at least partially translucent to a predetermined spectrum of ultraviolet light. In one embodiment the bow 250 has a critical section 255, in the contact region of the temple, which is more translucent to a predetermined spectrum of ultraviolet light than is the remainder of the bow 250. The length of the translucent section 255 is preferably 3-5 cm long but lengths of 2-7 cm would also function well. The transition between the translucent section 255 and the less translucent sections of the bow 250 is preferably not sudden but rather graded. In the preferred embodiment the nose bridge is at least partially translucent to a predetermined spectrum of ultraviolet light. The critical sections 255 may be of different thicknesses than other sections of the bows 250. In one example, the critical section 255 may be generally thinner than other sections of the bows 250 and pass more UV light.

Figure 17:
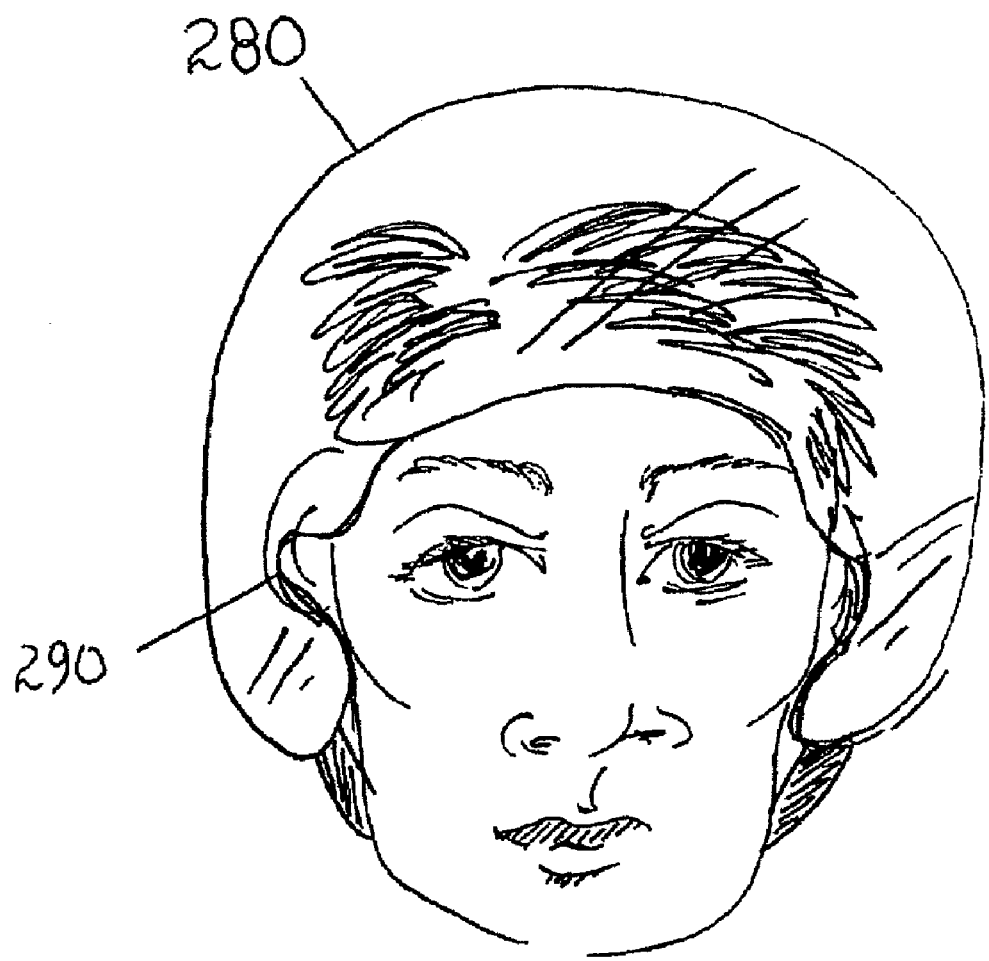
FIG. 17 shows the snow boarder gas filled hat.

FIG. 17 shows the snow boarder gas filled hat 280 with a safety channel 290 around the ears to provide hearing for safety. The hat is filled permanently with multiple chambers such as shown in FIG. 14. Alternatively, the whole hat is one chamber with tension pylons spaced every 1.5 cm to prevent bulging. Preferably the size is chosen for a tight fit to the head so that the portions extending down near the neck provide sufficient means for securement to the head. Alternatively, a strap is provided which itself is preferably transparent.

Another embodiment of the invention is a tent that passes UV and visible light but blocks ultra-violet. This would warm up during the day yet retain the heat of the inhabitants at night.

It should be understood that the foregoing relates only to preferred embodiments of the present invention, and that many changes and modifications can be made therein without departing from the spirit and scope of the invention as defined in the following claims.

We claim:

1. A pair of glasses comprising:
a first lens and a second lens;
a frame adapted to hold and secure the first lens and the second lens;
a first bow and a second bow being attached to the frame and being adapted to be secured to ears of a wearer of the glasses; and
wherein the first bow and the second bow are at least partially translucent to a spectrum of electromagnetic radiation.

2. The glasses of claim 1 wherein the frame is substantially opaque to the spectrum of electromagnetic radiation.

3. The glasses of claim 1 wherein the frame is at least partially translucent to the spectrum of electromagnetic radiation at a brow line of the wearer of the glasses.

4. The glasses of claim 1 wherein the spectrum of electromagnetic radiation comprises only selected frequencies.

5. The glasses of claim 1 wherein the first lens and the second lens are coupled together with a nose bridge.

6. The glasses of claim 5 wherein the nose bridge is at least partially translucent to the spectrum of electromagnetic radiation.

7. The glasses of claim 1 wherein the spectrum of electromagnetic radiation is in the ultraviolet-B range.

8. The glasses of claim 1 wherein the spectrum of electromagnetic radiation is in the ultraviolet range.

9. The glasses of claim 1 wherein the first bow and the second bow contain polyvinylidene fluoride.

10. The glasses of claim 1 wherein the first bow and the second bow contain a polyamide polymer.

11. The glasses of claim 1 wherein the first bow comprises a first critical section and the second bow comprises a second critical section, the first critical section and the second critical section being adapted to be at least partially in contact with the temple area of the wearer of the glasses.

12. The glasses of claim 11 wherein the first critical section is adapted to be more translucent to the spectrum of electromagnetic radiation than other areas of the first bow and the second critical section is adapted to be more translucent to the spectrum of electromagnetic radiation than other areas of the second bow.

13. The glasses of claim 12 wherein the first critical section is generally thinner than other areas of the first bow and the second critical section is generally thinner than other areas of the second bow.

14. The glasses of claim 1 wherein the first lens and the second lens are adapted to provide protection from at least some of the electromagnetic radiation.

15. The glasses of claim 1 wherein the first lens comprise a first corrective lens and the second lens comprises a second corrective lens.

16. The glasses of claim 1 wherein the first bow and the second bow each have a first section and a second section and wherein the first section is generally thicker than the second section.

17. The glasses of claim 16 wherein the second section is more translucent to the spectrum of electromagnetic radiation than the first section.

18. A pair of glasses comprising:
a first lens and a second lens;
a partial frame adapted to at least partially hold and secure the first lens and the second lens;
a first bow being attached to the first lens and a second bow being attached to the second lens, the first bow and the second bow being adapted to be secured to ears of a wearer of the glasses; and
wherein the first bow and the second bow are at least partially translucent to a spectrum of electromagnetic radiation.

19. The glasses of claim 18 wherein the spectrum of electromagnetic radiation comprises only selected frequencies within the spectrum.

20. The glasses of claim 18 wherein the first lens and the second lens are coupled together with a nose bridge.

21. The glasses of claim 20 wherein the nose bridge is at least partially translucent to the electromagnetic radiation.

22. The glasses of claim 18 wherein the spectrum of electromagnetic radiation is in the ultraviolet-B range.

23. The glasses of claim 18 wherein the spectrum of electromagnetic radiation is in the ultraviolet range.

24. The glasses of claim 18 wherein the first bow and the second bow contain polyvinylidene fluoride.

25. The glasses of claim 18 wherein the first bow and the second bow contain a polyamide polymer.

26. The glasses of claim 18 wherein the first bow comprises a first critical section and the second bow comprises a second critical section, the first critical section and the second critical section being adapted to be at least partially in contact with the temple area of the wearer of the glasses.

27. The glasses of claim 26 wherein the first critical section is adapted to be more translucent to the spectrum of electromagnetic radiation than other areas of the first bow and the second critical section is adapted to be more translucent to the spectrum of electromagnetic radiation than other areas of the second bow.

28. The glasses of claim 27 wherein the first critical section is generally thinner than other areas of the first bow and the second critical section is generally thinner than other areas of the second bow.

29. The glasses of claim 18 wherein the first lens and the second lens are adapted to provide protection from at least some of the spectrum of electromagnetic radiation.

30. The glasses of claim 18 wherein the first lens comprises a first corrective lens and the second lens comprises a second corrective lens.

31. The glasses of claim 18 wherein the first bow and the second bow each have a first section and a second section and wherein the first section is generally thicker than the second section.

32. The glasses of claim 31 wherein the second section is more translucent to the spectrum of electromagnetic radiation than the first section.

* * * * *